(12) United States Patent
von Deyn et al.

(10) Patent No.: US 7,563,921 B2
(45) Date of Patent: Jul. 21, 2009

(54) 2-CYANO-3(HALO)ALKOXY-BENZENESULFONAMIDE COMPOUNDS FOR COMBATING ANIMAL PESTS

(75) Inventors: Wolfgang von Deyn, Neustadt (DE); Henricus Maria Martinus Bastiaans, Usingen (DE); Matthias Pohlman, Heidelberg (DE); Michael Rack, Heidelberg (DE); Ernst Baumann, Dudenhofen (DE); Michael Puhl, Lampertheim (DE); Michael Hofmann, Ludwigshafen (DE); Livio Tedeschi, Mannheim (DE); Markus Kordes, Frankenthal (DE); Christopher Koradin, Ludwigshafen (DE); Douglas D. Anspaugh, Apex, NC (US); Deborah L. Culbertson, Fuquay-Varina, NC (US); Henry van Tuyl Cotter, Raleigh, NC (US); Hassan Oloumi-Sadeghi, Raleigh, NC (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 12/137,624

(22) Filed: Jun. 12, 2008

(65) Prior Publication Data
US 2008/0306297 A1 Dec. 11, 2008

Related U.S. Application Data

(62) Division of application No. 11/791,398, filed as application No. PCT/EP2005/012561 on Nov. 24, 2005.

(60) Provisional application No. 60/631,204, filed on Nov. 26, 2004.

(51) Int. Cl.
| | |
|---|---|
| C07C 319/20 | (2006.01) |
| C07C 323/32 | (2006.01) |
| C07C 311/15 | (2006.01) |
| A01N 25/00 | (2006.01) |
| A01N 25/26 | (2006.01) |
| A01P 17/00 | (2006.01) |
| A61K 31/18 | (2006.01) |

(52) U.S. Cl. ..................................... 558/317; 558/412
(58) Field of Classification Search ....................... None
See application file for complete search history.

(56) References Cited

U.S. PATENT DOCUMENTS

| 3,997,603 A | 12/1976 | Martin et al. |
| 4,379,157 A | 4/1983 | Van Hes et al. |
| 2002/0072626 A1 | 6/2002 | Kantor et al. |

FOREIGN PATENT DOCUMENTS

| EP | 0 033 984 | 8/1981 |
| WO | WO 01/42198 | 6/2001 |

OTHER PUBLICATIONS

Farina et al., Chemical Abstracts, 87:184305, 1977, Registry No. 64572-57-2.*
Office Action dated Jun. 18, 2008, in corresponding prior U.S. Appl. No. 11/791,398, filed May 23, 2008.

* cited by examiner

Primary Examiner—Fiona T Powers
(74) Attorney, Agent, or Firm—Brinks Hofer Gilson & Lione

(57) ABSTRACT

The invention relates to 2-cyano-3-(halo)alkoxy-benzenesulfonamide compounds I

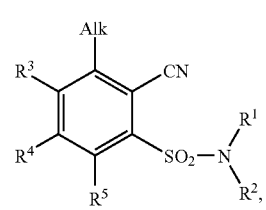

where the variables Alk and $R^1$ to $R^5$ are as defined in claim 1, and/or to their agriculturally useful salts.

Moreover, the present invention relates to
the use of compounds I and/or their salts for combating animal pests;
agricultural compositions comprising such an amount of at least one compound of the general formula I and/or at least one agriculturally useful salt of I and at least one inert liquid and/or solid agronomically acceptable carrier that it has a pesticidal action and, if desired, at least one surfactant; and
a method of combating animal pests which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a pesticidally effective amount of at least one 2-cyano-3-(halo)alkoxy-benzenesulfonamide compound of the formula I and/or at least one agriculturally acceptable salt thereof.
a method for the for the protection of seeds from soil insects and of the resulting plant's roots and shoots from soil and foliar insects comprising contacting the seeds before sowing and/or after pregermination with a 2-cyano-3-(halo)alkoxy-benzenesulfonamide compound of the general formula I.

1 Claim, No Drawings

2-CYANO-3(HALO)ALKOXY-BENZENESULFONAMIDE COMPOUNDS FOR COMBATING ANIMAL PESTS

This application is a Divisional of U.S. application Ser. No. 11/791,398, now allowed, filed May 23, 2007 which is the National Stage in the U.S. of International Application No. PCT/EP2005/012561 filed Nov. 24, 2005, which claims the benefit of U.S. Provisional Application No. 60/631,204, filed Nov. 26, 2004, the entire contents of these application are hereby incorporated herein by reference.

The present invention relates to 2-cyano-3-(halo)alkoxy-benzenesulfonamide compounds and to the agriculturally useful salts thereof and to compositions comprising such compounds. The invention also relates to the use of the 2-cyano-3-(halo)alkoxy-benzenesulfonamide compounds, of their salts or of compositions comprising them for combating animal pests.

Animal pests destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating animal pests. In particular, animal pests such as insects and acaridae are difficult to be effectively controlled.

EP-A 033 984 describes substituted 2-cyanobenzenesulfonamide compounds having an aphicidal activity. The benzenesulfonamide compounds carry, inter alia, a fluorine or chorine atom or a methyl group in the 3-position of the phenyl ring. Also disclosed is 2-cyano-5-trifluoromethoxy-N,N-dimethylbenzenesulfonamide. However, the pesticidal activity of said compounds is unsatisfactory and they are only taught to be active against aphids.

Therefore, it has been an object of the present invention to provide compounds having a good pesticidal activity, especially against difficult to control insects and acaridae.

It has been found that these objects are solved by the 2-cyano-3-(halo)alkoxy-benzenesulfonamide compounds of formula I

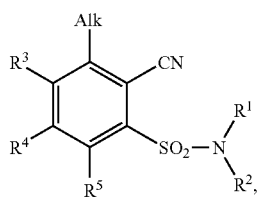

I where
Alk is $C_1$-$C_4$-alkoxy or $C_1$-$C_4$-haloalkoxy;
$R^1$ is $C_1$-$C_6$-alkyl or $C_2$-$C_6$-alkenyl;
$R^2$ is $C_1$-$C_6$-alkyl, $C_2$-$C_6$-alkenyl, $C_2$-$C_6$-alkinyl, $C_3$-$C_8$-cycloalkyl or $C_1$-$C_4$-alkoxy, wherein the five last-mentioned radicals may be unsubstituted, partially or fully halogenated and/or may carry one, two, or three radicals selected from the group consisting of hydroxy, $C_1$-$C_4$-alkoxy, $C_1$-$C_4$-alkylthio, $C_1$-$C_4$-alkylsulfinyl, $C_1$-$C_4$-alkylsulfonyl, $C_1$-$C_4$-haloalkoxy, $C_1$-$C_4$-haloalkylthio, $C_1$-$C_4$-alkoxycarbonyl, cyano, amino, ($C_1$-$C_4$-alkyl)amino, di-($C_1$-$C_4$-alkyl)amino, $C_3$-$C_8$-cycloalkyl and phenyl, it being possible for phenyl to be unsubstituted, partially or fully halogenated and/or to carry one, two or three substituents selected from the group consisting of $C_1$-$C_4$-alkyl, $C_1$-$C_4$-haloalkyl, $C_1$-$C_4$-alkoxy, $C_1$-$C_4$-haloalkoxy; and
$R^3$, $R^4$ and $R^5$ are independently of one another selected from the group consisting of hydrogen, halogen, cyano, nitro, $C_1$-$C_6$-alkyl, $C_3$-$C_8$-cycloalkyl, $C_1$-$C_4$-haloalkyl, $C_1$-$C_4$-alkoxy, $C_1$-$C_4$-alkylthio, $C_1$-$C_4$-alkylsulfinyl, $C_1$-$C_4$-alkylsulfonyl, $C_1$-$C_4$-haloalkoxy, $C_1$-$C_4$-haloalkylthio, $C_2$-$C_6$-alkenyl, $C_2$-$C_6$-alkinyl, $C_1$-$C_4$-alkoxycarbonyl, amino, ($C_1$-$C_4$-alkyl)amino, di-($C_1$-$C_4$-alkyl)amino, aminocarbonyl, ($C_1$-$C_4$-alkyl)aminocarbonyl and di-($C_1$-$C_4$-alkyl)aminocarbonyl;

and by their agriculturally acceptable salts.

The compounds of formula I and their agriculturally acceptable salts have a high pesticidal activity, especially against difficult to control insects and acaridae.

Accordingly, the present invention relates to novel 2-cyano-3-(halo)alkoxy-benzenesulfonamide compounds of the formula I and to their agriculturally useful salts.

Moreover, the present invention relates to
the use of compounds I and/or their salts for combating animal pests;
agricultural compositions comprising such an amount of at least one 2-cyano-3-(halo)alkoxy-benzenesulfonamide compound of the formula I and/or at least one agriculturally useful salt of I and at least one inert liquid and/or solid agronomically acceptable carrier that it has a pesticidal action and, if desired, at least one surfactant; and
a method of combating animal pests which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a pesticidally effective amount of at least one 2-cyano-3-(halo)alkoxy-benzenesulfonamide compound of the formula I and/or at least one agriculturally acceptable salt thereof.
a method for the for the protection of seeds from soil insects and of the resulting plant's roots and shoots from soil and foliar insects comprising contacting the seeds before sowing and/or after pregermination with a 2-cyano-3-(halo)alkoxy-benzenesulfonamide compound of the general formula I In the variables Alk and $R^1$ to $R^5$, the compounds of formula I may have one or more centers of chirality, in which case they are present as mixtures of enantiomers or diastereomers. The present invention provides both the pure enantiomes or diastereomers or mixtures thereof.

Salts of the compounds of the formula I which are suitable for the use according to the invention are especially agriculturally acceptable salts. They can be formed in a customary method, e.g. by reacting the compound with an acid of the anion in question.

Suitable agriculturally useful salts are especially the salts of those cations or the acid addition salts of those acids whose cations and anions, respectively, do not have any adverse effect on the action of the compounds according to the present invention, which are useful for combating harmful insects or arachnids. Thus, suitable cations are in particular the ions of the alkali metals, preferably lithium, sodium and potassium, of the alkaline earth metals, preferably calcium, magnesium and barium, and of the transition metals, preferably manganese, copper, zinc and iron, and also the ammonium ion which may, if desired, carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl) sulfonium, and sulfoxonium ions, preferably tri($C_1$-$C_4$-alkyl) sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of the formulae I with an acid of the corresponding anion, preferably of hydrochloric acid, hydrobromic acid, sulfuric acid, phosphoric acid or nitric acid.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine.

Examples of other meanings are:

The term "$C_1$-$C_4$-alkyl" as used herein and the alkyl moieties of alkylamino and dialkylamino refer to a saturated straight-chain or branched hydrocarbon radical having 1 to 4 carbon atoms, i.e., for example methyl, ethyl, propyl, 1-methylethyl, butyl, 1-methylpropyl, 2-methylpropyl or 1,1-dimethylethyl.

The term "$C_1$-$C_6$-alkyl" as used herein refers to a saturated straight-chain or branched hydrocarbon radical having 1 to 6 carbon atoms, for example one of the radicals mentioned under $C_1$-$C_4$-alkyl and also n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl.

The term "$C_1$-$C_4$-haloalkyl" as used herein refers to a straight-chain or branched saturated alkyl radical having 1 to 4 carbon atoms (as mentioned above), where some or all of the hydrogen atoms in these radicals may be replaced by fluorine, chlorine, bromine and/or iodine, i.e., for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl.

The term "$C_1$-$C_4$-alkoxy" as used herein refers to a straight-chain or branched saturated alkyl radical having 1 to 4 carbon atoms (as mentioned above) which is attached via an oxygen atom, i.e., for example methoxy, ethoxy, n-propoxy, 1-methylethoxy, n-butoxy, 1-methylpropoxy, 2-methylpropoxy or 1,1-dimethylethoxy.

The term "$C_1$-$C_4$-haloalkoxy" as used herein refers to a $C_1$-$C_4$-alkoxy radical as mentioned above which is partially or fully substituted by fluorine, chlorine, bromine and/or iodine, i.e., for example, chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy.

The term "$C_1$-$C_4$-alkylthio" ($C_1$-$C_4$-alkyl-S—) as used herein refers to a straight-chain or branched saturated alkyl radical having 1 to 4 carbon atoms (as mentioned above) which is attached via a sulfur atom, i.e., for example methylthio, ethylthio, n-propylthio, 1-methylethylthio, butylthio, 1-methylpropylthio, 2-methylpropylthio or 1,1-dimethylethylthio.

The term "$C_1$-$C_4$-haloalkylthio" ($C_1$-$C_4$-haloalkyl-S—) as used herein refers to a straight-chain or branched saturated alkyl radical having 1 to 4 carbon atoms (as mentioned above), where some or all of the hydrogen atoms in these radicals may be replaced by fluorine, chlorine, bromine and/or iodine, i.e., for example chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio or nonafluorobutylthio.

The term "$C_1$-$C_4$-alkylsulfinyl" ($C_1$-$C_4$-alkyl-S(=O)—), as used herein refers to a straight-chain or branched saturated hydrocarbon radical (as mentioned above) having 1 to 4 carbon atoms bonded through the sulfur atom of the sulfinyl group at any bond in the alkyl radical, i.e., for example $SO_2$—$CH_3$, $SO_2$—$C_2H_5$, n-propylsulfinyl, 1-methylethylsulfinyl, n-butylsulfinyl, 1-methylpropylsulfinyl, 2-methylpropylsulfinyl, 1,1-dimethylethylsulfinyl, n-pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl or 1-ethylpropylsulfinyl.

The term "$C_1$-$C_4$-alkylsulfonyl" ($C_1$-$C_4$-alkyl-S(=O)$_2$—) as used herein refers to a straight-chain or branched saturated alkyl radical having 1 to 4 carbon atoms (as mentioned above) which is bonded via the sulfur atom of the sulfonyl group at any bond in the alkyl radical, i.e., for example $SO_2$—$CH_3$, $SO_2$—$C_2H_5$, n-propylsulfonyl, $SO_2$—$CH(CH_3)_2$, n-butylsulfonyl, 1-methylpropylsulfonyl, 2-methylpropylsulfonyl or $SO_2$—$C(CH_3)_3$.

The term "$C_1$-$C_4$-alkoxycarbonyl" as used herein refers to a straight-chain or branched alkoxy radical (as mentioned above) having 1 to 4 carbon atoms attached via the carbon atom of the carbonyl group, i.e., for example methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl or 1,1-dimethylethoxycarbonyl.

The term "($C_1$-$C_4$-alkyl)amino" as used herein refers to, for example, methylamino, ethylamino, n-propylamino, 1-methylethylamino, n-butylamino, 1-methylpropylamino, 2-methylpropylamino or 1,1-dimethylethylamino.

The term "($C_1$-$C_4$-alkyl)aminocarbonyl" ($C_1$-$C_4$-alkyl-NH—CO—) as used herein refers to, for example, methyl-NH—CO—, ethyl-NH—CO—, n-propyl-NH—CO—, 1-methylethyl-NH—CO—, n-butyl-NH—CO—, 1-methylpropyl-NH—CO—, 2-methylpropyl-NH—CO— or 1,1-dimethylethyl-NH—CO—.

The term "di-($C_1$-$C_4$-alkyl)amino" as used herein refers to, for example, N,N-dimethylamino, N,N-diethylamino, N,N-di-(1-methylethyl)amino, N,N-dipropylamino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl) amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl) amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl) amino, N-(1,1-dimethylethyl)-N-(1-methylpropyl)amino or N-(1,1-dimethylethyl)-N-(2-methylpropyl)amino.

The term "di-($C_1$-$C_4$-alkyl)aminocarbonyl" (di-($C_1$-$C_4$-alkyl)amino-CO—) as used herein refers to, for example, N,N-dimethylamino-CO—, N,N-diethylamino-CO—, N,N-di-(1-methylethyl)amino-CO—, N,N-dipropylamino-CO—, N,N-dibutylamino-CO—, N,N-di-(1-methylpropyl)amino-CO—, N,N-di-(2-methylpropyl)amino-CO—, N,N-di-(1,1-dimethylethyl)amino-CO—, N-ethyl-N-methylamino-CO—, N-methyl-N-propylamino-CO—, N-methyl-N-(1-methylethyl)amino-CO—, N-butyl-N-methylamino-CO—, N-methyl-N-(1-methylpropyl)amino-CO—, N-methyl-N-(2-methylpropyl)amino-CO—, N-(1,1-dimethylethyl)-N-methylamino-CO—, N-ethyl-N-propylamino-CO—, N-ethyl-N-(1-methylethyl)amino-CO—, N-butyl-N-ethylamino-CO—, N-ethyl-N-(1-methylpropyl)amino-CO—, N-ethyl-N-(2-methylpropyl)amino-CO—, N-ethyl-N-(1,1-dimethylethyl)amino-CO—, N-(1-methylethyl)-N-propylamino-CO—, N-butyl-N-propylamino-CO—, N-(1-methylpropyl)-N-propylamino-CO—, N-(2-methylpropyl)-N-propylamino-CO—, N-(1,1-dimethylethyl)-N-propylamino-CO—, N-butyl-N-(1-methylethyl)amino-CO—, N-(1-methylethyl)-N-(1-methylpropyl)amino-CO—, N-(1-methylethyl)-N-(2-methylpropyl)amino-CO—, N-(1,1-dimethylethyl)-N-(1-methylethyl)amino-CO—, N-butyl-N-(1-methylpropyl)amino-CO—, N-butyl-N-(2-methylpropyl) amino-CO—, N-butyl-N-(1,1-dimethylethyl)amino-CO—, N-(1-methylpropyl)-N-(2-methylpropyl)amino-CO—, N-(1,1-dimethylethyl)-N-(1-methylpropyl)amino-CO— or N-(1,1-dimethylethyl)-N-(2-methylpropyl)amino-CO—.

The term "$C_2$-$C_6$-alkenyl" as used herein refers to a straight-chain or branched monounsaturated hydrocarbon radical having 2 to 6 carbon atoms and a double bond in any position, i.e., for example ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_6$-alkynyl" as used herein refers to a straight-chain or branched aliphatic hydrocarbon radical which contains a C—C triple bond and has 2 to 6 carbons atoms: for example ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "$C_3$-$C_8$-cycloalkyl" as used herein refers to a monocyclic hydrocarbon radical having 3 to 8 carbon atoms, for example cyclopropyl, cyclobutyl, cyclopentyl, cyclohexyl, cycloheptyl or cyclooctyl.

Among the 2-cyano-3-(halo)alkoxy-benzenesulfonamide compounds of formula I, preference is given to those in which the variables Alk, $R^1$ and $R^2$, independently of one another, but in particular in combination, have the meanings given below:

Alk is Methoxy, Ethoxy, Difluoromethoxy, Trifluoromethoxy or Chlorodifluoromethoxy;

$R^1$ is $C_1$-$C_4$-alkyl, especially methyl or ethyl;

$R^2$ is $C_1$-$C_4$-alkyl, $C_1$-$C_4$-haloalkyl, $C_1$-$C_4$-alkoxy-$C_1$-$C_4$-alkyl, $C_1$-$C_4$-alkylthio-$C_1$-$C_4$-alkyl, $C_2$-$C_4$-alkinyl or $C_3$-$C_6$-cycloalkyl, in particular methyl, ethyl, 1-methylethyl, cyclopropyl, 2-methoxy-ethyl, 2-methylthio-ethyl or prop-2-yn-1-yl.

A preferred embodiment of the present invention relates to 2-cyano-3-(halo)alkoxy-benzenesulfonamide compounds of the formula I where the moiety —NR1R2 has the following meanings:

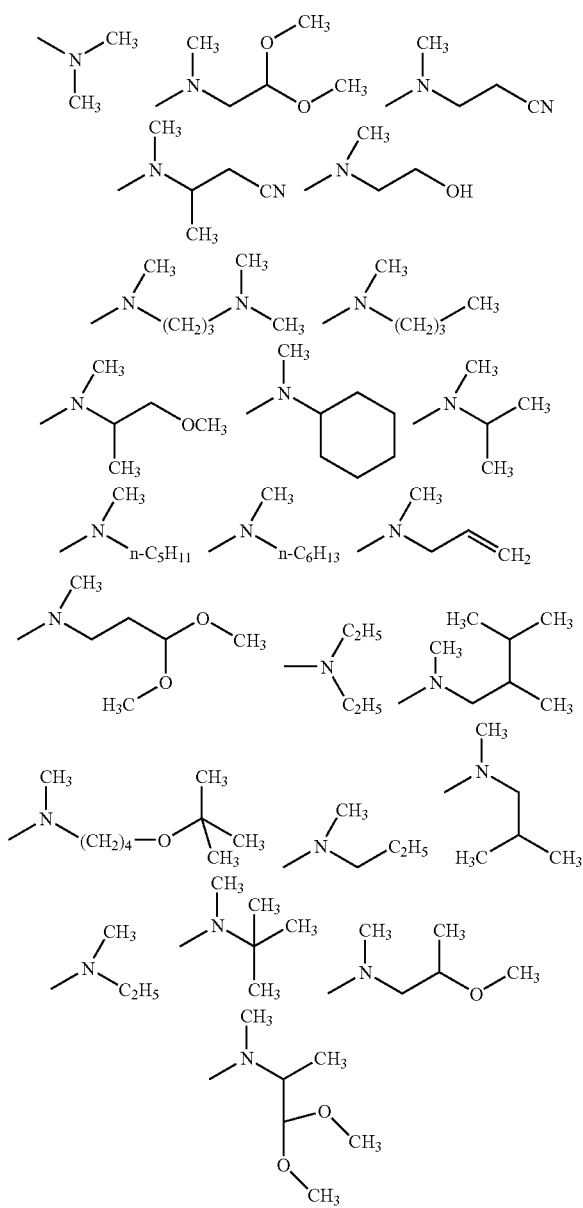

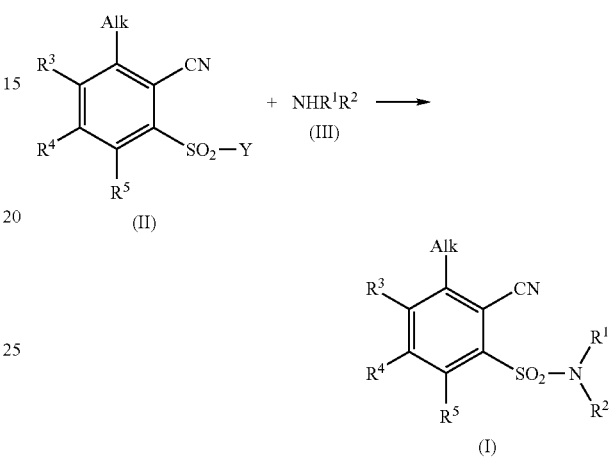

Another preferred embodiment of the present invention relates to 2-cyano-3-(halo)alkoxy-benzenesulfonamide compounds of the formula I where the variables $R^1$ and $R^2$ have the meanings mentioned above and in particular the meanings given as being preferred and at least one of the radicals $R^3$, $R^4$ or $R^5$ is different from hydrogen. Preferably one or two of the radicals $R^3$, $R^4$ and $R^5$ represent hydrogen, wherein more preferably $R^4$ represents hydrogen. Amongst these compounds preference is given to those compounds wherein $R^3$ is different from hydrogen and preferably represents halogen, especially chlorine or fluorine, and the other radicals $R^4$ and $R^5$ are hydrogen. Other preferred compounds are those wherein $R^5$ is different from hydrogen and preferably represents halogen, especially chlorine or fluorine, and the other radicals $R^4$ and $R^3$ are hydrogen.

Another preferred embodiment of the present invention relates to 2-cyano-3-(halo)alkoxy-benzenesulfonamide compounds of the formula I where the variables $R^1$ and $R^2$ have the meanings mentioned above and in particular the meanings given as being preferred and each of the radicals $R^3$, $R^4$ and $R^5$ represent hydrogen.

The 2-cyano-3-(halo)alkoxy-benzenesulfonamide compounds of the formula I can be prepared, for example, by reacting a 2-cyanobenzenesulfonylhalide II with ammonia or a primary amine (III), similarly to a process described in J. March, 4$^{th}$ edition 1992, p. 499 (see Scheme 1).

Scheme 1:

In Scheme 1 the variables Alk and $R^1$ to $R^5$ are as defined above and Y is halogen, especially chlorine or bromine. The reaction of a sulfonylhalide II, especially a sulfonylchloride, with an amine III is usually carried out in the presence of a solvent. Suitable solvents are polar solvents which are inert under the reaction conditions, for example $C_1$-$C_4$-alkanols such as methanol, ethanol, n-propanol or isopropanol, dialkyl ethers such as diethyl ether, diisopropyl ether or methyl tert-butyl ether, cyclic ethers such as dioxane or tetrahydrofuran, acetonitrile, carboxamides such as N,N-dimethyl formamide, N,N-dimethyl acetamide or N-methylpyrrolidinone, water, (provided the sulfonylhalide II is sufficiently resistent to hydrolysis under the reaction conditions used) or a mixture thereof.

In general, the amine III is employed in an at least equimolar amount, preferably at least 2-fold molar excess, based on the sulfonylhalide II, to bind the hydrogen halide formed. It may be advantageous to employ the primary amine III in an up to 6-fold molar excess, based on the sulfonylhalide II.

It may be advantageous to carry out the reaction in the presence of an auxiliary base. Suitable auxiliary bases include organic bases, for example tertiary amines, such as aliphatic tertiary amines, such as trimethylamine, triethylamine or diisopropylamine, cycloaliphatic tertiary amines such as N-methylpiperidine or aromatic amines such as pyridine, substituted pyridines such as 2,3,5-collidine, 2,4,6-collidine, 2,4-lutidine, 3,5-lutidine or 2,6-lutidine, and inorganic bases, for example alkali metal carbonates and alkaline earth metal carbonates such as lithium carbonate, potassium carbonate and sodium carbonate, calcium carbonate and alkaline metal hydrogencarbonates such as sodium hydrogen carbonate.

The molar ratio of auxiliary base to sulfonylhalide II is preferably in the range of from 1:1 to 4:1, preferably 1:1 to 2:1. If the reaction is carried out in the presence of an auxiliary base, the molar ratio of primary amine III to sulfonylhalide II usually is 1:1 to 1.5:1.

In general, the reaction is carried out at a reaction temperature ranging from 0° C. to the boiling point of the solvent, preferably from 0 to 30° C.

If not commercially available, the sulfonylhalide compounds II where the variables Alk and $R^3$ to $R^5$ are as defined above may be prepared, for example by one of the processes as described below.

Scheme 2:

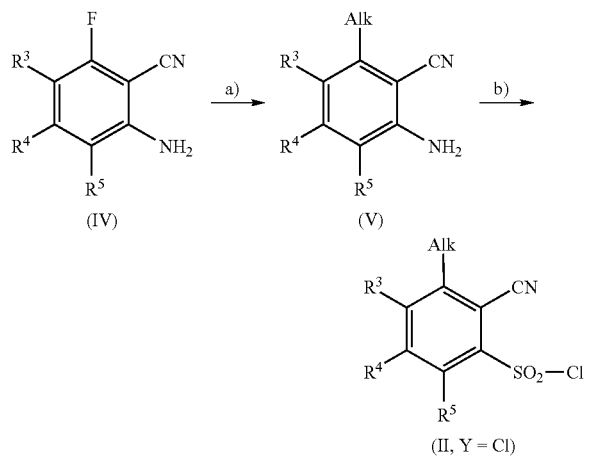

2-Amino-6-fluoro-benzonitrile is commercially available or can be prepared according to U.S. Pat. No. 4,504,660.

a) Conversion of the 2-amino-6-fluoro-benzonitriles IV to the alkoxy analogues V by reacting IV with an appropriate alkoxide such as sodium methoxide and sodium ethoxide is preferably carried out in an inert organic solvent, for example an ether such as diethyl ether, diisopropyl ether, tetrahydrofuran, dioxane, or in the respective alcohol, or in a carboxamide such as N,N-dimethyl formamide, N,N-dimethyl acetamide or N-methylpyrrolidinone, or in dimethylsulfoxide or in a mixture of the above mentioned solvents.

The amount of alkoxide should preferable be about equimolar to the amount of IV. However, also an excess of alkoxide from about 100 to 300 molar-%, based on the amount of IV, can be applied in order to accelerate the conversion.

A suitable temperature range is from 0 to 120° C., in particular 50 to 100° C.

b) subsequent conversion of the amino group of the compound V into the corresponding diazonium group followed by reacting the diazonium salt with sulfur dioxide in the presence of copper(II) chloride to afford the sulfonylchloride II. Suitable nitrosating agents are nitrosonium tetrafluoroborate, nitrosyl chloride, nitrosyl sulfuric acid, alkyl nitriles such as tert.-butyl nitrile, or salts of nitrous acid such as sodium nitrite. Preferably, sodium nitrite is used as nitrous acid salt.

In general, the sulfur dioxide is dissolved in glacial acetic acid.

The compounds of formula V may also be prepared according to methods described in WO 94/18980 using ortho-nitroanilines as precursors or in WO 00/59868 using isatin precursors.

Scheme 3:

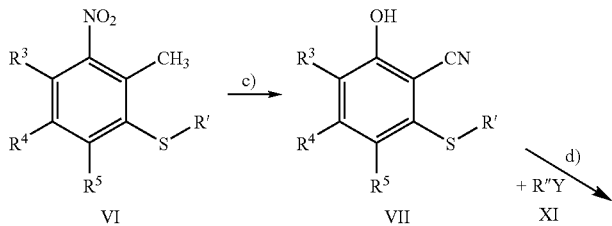

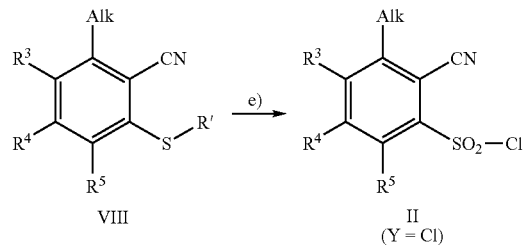

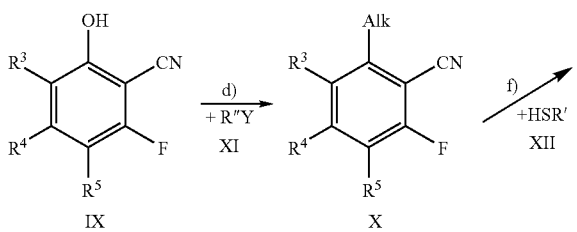

2-Methyl-3-nitro-phenylthioether VI can be prepared according to the methods described in WO 00/29394.

c) The transformation of VI (R'=$C_1$-$C_6$-alkyl or benzyl) into the 2-cyanophenol compound VII is e.g. achieved by reacting a 2-methyl-3-nitro-phenylthioether VI with an organic nitrite R—ONO, wherein R is alkyl, preferable $C_1$-$C_6$-alkyl, in the presence of a base. Suitable nitrites are $C_2$-$C_8$-alkyl nitrites such as n-butyl nitrite or (iso)amyl nitrite. Suitable bases are alkali metal alkoxides such as sodium methoxide, potassium methoxide or potassium tert-butoxide, alkali metal hydroxides such as NaOH or KOH.

The reaction is usually carried out in an inert solvent, which preferably comprises a polar aprotic solvent. Suitable polar aprotic solvents include carboxamides such as N,N-dialkylformamides, e.g. N,N-dimethylformamide, N,N-dialkylacetamides, e.g. N,N-dimethylacetamide or N-alkyllactames e.g. N-methylpyrrolidone or mixtures thereof, or mixtures thereof with non-polar solvents such as alkanes, cycloalkanes and aromatic solvents, e.g. toluene and xylenes.

When using sodium bases, 1-10 mol % of an alcohol may be added, if appropriate. The stoichiometric ratios are, for example, as follows: 1-4 equivalents of base, 1-2 equivalents of R—ONO; preferably 1.5-2.5 equivalents of base and 1-1.3 equivalents of R—ONO; equally preferably: 1-2 equivalents of base and 1-1.3 equivalents of R—ONO.

The reaction is usually carried out in the range from (−60)° C. to room temperature, preferably (−40)° C. to 0° C., in particular from (−30)° C. to (−10)° C.

d) Alkylation of the phenol VII or IX in analogy to a process described in WO 99/14187 by reacting VII or IX with an alkylating agent XI, R"Y (R"=$C_1$-$C_4$-alkyl or $C_1$-$C_4$-haloalkyl), were Y is halogen, especially chlorine or bromine, in the presence of a base.

Suitable bases are alkali metal alkoxides such as sodium methoxide, potassium methoxide or potassium tert-butoxide, alkali metal hydroxides such as sodium hydroxide or potassium hydroxide.

The reaction is usually carried out in an inert solvent, for example an ether such as diethyl ether, diisopropyl ether, tetrahydrofuran, ethylen glycol dimethylether, dioxane, or in a carboxamide such as N,N-dimethyl formamide, N,N-dimethyl acetamide or N-methylpyrrolidinone or in dimethylsulfoxide or in a mixture of the above mentioned solvents.

e) Transformation of thioether VII into sulfonylchloride II (Y=Cl) in analogy to a process described in WO 96/33167 by reacting VII with chlorine in a suitable solvent, for example chlorobenzene or dichloromethane in the presence of water.

f) Transformation of fluorobenzene X into thioether VIII (R'=$C_1$-$C_6$-alkyl or benzyl) by reacting with alkyl- or benzylthiol XII in the presence of a base. Suitable bases are alkali metal alkoxides such as sodium methoxide, potassium methoxide or potassium tert-butoxide, alkali metal hydroxides such as sodium hydroxide or potassium hydroxide.

The reaction is usually carried out in a solvent, for example an ether such as diethyl ether, diisopropyl ether, tetrahydrofuran, ethylen glycol dimethylether, dioxane, or in a carboxamide such as N,N-dimethyl formamide, N,N-dimethyl acetamide or N-methylpyrrolidinone or in dimethylsulfoxide or in water. It may also be possible to work in an excess of the alkyl- or benzylthiol, which then serves as solvent.

Unless otherwise specified, all processes described above are expediently carried out under atmospheric pressure or under the inherent autogeneous pressure of the reaction mixture in question. In general, the reactants are employed in a molar ratio of from 0.95:1 to 5:1.

If individual compounds I cannot be obtained via the above-described routes, they can be prepared by derivatization of other compounds I or by customary modifications of the synthesis routes described.

The reaction mixtures are worked up in the customary manner, for example by mixing with water, separating the phases and, if appropriate, purifying the crude products by chromatography, for example on alumina or silica gel. Some of the intermediates and end products may be obtained in the form of colorless or pale brown viscous oils which are freed or purified form volatile components under reduced pressure and at moderately elevated temperature. If the intermediates and end products are obtained as solids, they may be purified by recrystallisation or digestion.

The 2-cyano-3-(halo)alkoxy-benzenesulfonamide compounds I can be obtained from their preparation as isomer mixtures which, however, can be separated into the pure isomers, if desired, by the methods customary for this purpose, such as crystallization or chromatography, also on an optically active adsorbate. Pure optically active isomers can be prepared advantageously from suitable optically active starting materials.

Due to their excellent activity, the 2-cyano-3-(halo)alkoxy-benzenesulfonamide compounds of the formula I may be used for controlling animal pests. Animal pests include harmful insects and acaridae. Accordingly, the invention further provides agriculturally composition for combating animal pests, especially insects and/or acaridae which comprises such an amount of at least one compound of the general formula I and/or at least one agriculturally useful salt of I and at least one inert liquid and/or solid agronomically acceptable carrier that it has a pesticidal action and, if desired, at least one surfactant.

Such a composition may contain a single active compound of the formula I or a mixture of several active compounds I according to the present invention. The composition according to the present invention may comprise an individual isomer or mixtures of isomers.

The 2-cyano-3-(halo)alkoxy-benzenesulfonamide compounds I and the pesticidical compositions comprising them are effective agents for controlling nematodes, insects and arachnids, especially insects, in crop protection. In particular, they are suitable for controlling the following animal pests:

insects from the order of the lepidopterans (Lepidoptera), for example *Agrotis upsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia* nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni and Zeiraphera canadensis;

beetles (Coleoptera), for example Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus and Sitophilus granaria;

dipterans (Diptera), for example Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea and Tipula paludosa;

thrips (Thysanoptera), e.g. Dichromothrips corbetti, Frankliniella fusca, Frankliniella occidentalis, Frankliniella tritici, Scirtothrips citri, Thrips oryzae, Thrips palmi and Thrips tabaci;

hymenopterans (Hymenoptera), e.g. Athalia rosae, Atta cephalotes, Atta sexdens, Atta texana, Hoplocampa minuta, Hoplocampa testudinea, Monomorium pharaonis, Solenopsis geminata and Solenopsis invicta;

heteropterans (Heteroptera), e.g. Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis and Thyanta perditor, homopterans (Homoptera), e.g. Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus homi, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus persicae, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Sogatella furcifera Trialeurodes vaporariorum, Toxoptera aurantiiand, and Viteus vitifolii, termites (Isoptera), e.g. Calotermes flavicollis, Leucotermes flavipes, Reticulitermes flavipes, Reticulitermes lucifugus und Termes natalensis;

orthopterans (Orthoptera), e.g. Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus and Tachycines asynamorus;

Arachnoidea, such as arachnids (Acarina), e.g. of the families Argasidae, Ixodidae and Sarcoptidae, such as Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei, and Eriophyidae spp. such as Aculus schlechtendali, Phyllocoptrata oleivora and Eriophyes sheldoni; Tarsonemidae spp. such as Phytonemus pallidus and Polyphagotarsonemus latus; Tenuipalpidae spp. such as Brevipalpus phoenicis; Tetranychidae spp. such as Tetranychus cinnabarinus, Tetranychus kanzawai, Tetranychus pacificus, Tetranychus telarius and Tetranychus urticae, Panonychus ulmi, Panonychus citri, and oligonychus pratensis;

Siphonatera, e.g. Xenopsylla cheopsis, Ceratophyllus spp.

The compounds of formula I are preferably used for controlling pests of the orders Homoptera and Thysanoptera.

The compounds of formula I or the pesticidal compositions comprising them may be used to protect growing plants and crops from attack or infestation by animal pests, especially insects or acaridae by contacting the plant/crop with a pesticidally effective amount of compounds of formula I. The term "crop" refers both to growing and harvested crops.

The animal pest, especially the insect, acaridae, plant and/or soil or water in which the plant is growing can be contacted with the present compound(s) I or composition(s) containing them by any application method known in the art. As such, "contacting" includes both direct contact (applying the compounds/compositions directly on the animal pest, especially the insect and/or acaridae, and/or plant—typically to the foliage, stem or roots of the plant) and indirect contact (applying the compounds/compositions to the locus of the animal pest, especially the insect and/or acaridae, and/or plant).

Moreover, animal pests, especially insects or acaridae may be controlled by contacting the target pest, its food supply or its locus with a pesticidally effective amount of compounds of formula I. As such, the application may be carried out before or after the infection of the locus, growing crops, or harvested crops by the pest.

"Locus" means a habitat, breeding ground, plant, seed, soil, area, material or environment in which a pest or parasite is growing or may grow.

Effective amounts suitable for use in the method of invention may vary depending upon the particular formula I compound, target pest, method of application, application timing, weather conditions, animal pest habitat, especially insect, or acarid habitat, or the like. In general, for use in treating crop plants, the rate of application of the compounds I and/or compositions according to this invention may be in the range of about 0.1 g to about 4000 g per hectare, desirably from about 25 g to about 600 g per hectare, more desirably from about 50 g to about 500 g per hectare. For use in treating seeds, the typical rate of application is of from about 1 g to about 500 g per kilogram of seeds, desirably from about 2 g to about 300 g per kilogram of seeds, more desirably from about 10 g to about 200 g per kilogram of seeds. Customary application rates in the protection of materials are, for example, from about 0.001 g to about 2000 g, desirably from about 0.005 g to about 1000 g, of active compound per cubic meter of treated material.

For use according to the present invention, the compounds I or the pesticidal compositions comprising them can be converted into the customary formulations, e.g. solutions, emulsions, microemulsions, suspensions, flowable concentrates, dusts, powders, pastes and granules. The use form depends on the particular purpose; in any case, it should guarantee a fine and uniform distribution of the compound according to the invention.

The pesticidal composition for combating animal pests, especially insects and/or acaridae contains such an amount of at least one compound of formula I or an agriculturally useful salt of I and auxiliaries which are usually used in formulating pesticidal composition.

The formulations are prepared in a known manner, e.g. by extending the active ingredient with solvents and/or carriers, if desired using emulsifiers and dispersants, it also being possible to use other organic solvents as auxiliary solvents if water is used as the diluent. Solvents/auxiliaries which are suitable are essentially:

water, aromatic solvents (for example Solvesso® products, xylene), chlorinated aromatics (e.g. chlorobenzenes), paraffins (e.g. mineral oil fractions), alcohols (e.g. methanol, butanol, pentanol, benzyl alcohol), ketones (e.g. cyclohexanone, gamma-butyrolactone), amines (e.g. ethanolamine, dimethylformamide), pyrrolidones (e.g. N-methylpyrrolidone or NOP), acetates (e.g. glycol diacetate), glycols, fatty acid dimethylamides, fatty acids and fatty acid esters.

In principle, solvent mixtures may also be used.

carriers such as ground natural minerals (e.g. kaolins, clays, talc, chalk) and ground synthetic minerals (e.g. highly-disperse silica, silicates); emulsifiers such as non-ionic and anionic emulsifiers (e.g. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of napthalenesulfonic acid with phenol or formaldehyde, polyoxyethylene octylphenyl ether, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, e.g. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, e.g. dimethylformamide, dimethyl sulfoxide, N-methylpyrrolidone and water.

Powders, materials for scattering and dusts can be prepared by mixing or concomitantly grinding the active substances with a solid carrier.

Granules, e.g. coated granules, compacted granules, impregnated granules and homogeneous granules, can be prepared by binding the active ingredients to solid carriers. Examples of solid carriers are mineral earths, such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, e.g. ammonium sulfate, ammonium phosphate, ammonium nitrate,ureas, and products of vegetable origin, such as cereal meal, tree bark meal, wood meal and nutshell meal, cellulose powders and other solid carriers.

Such formulations or compositions of the present invention include a formula I compound of this invention (or combinations thereof admixed with one or more agronomically acceptable inert, solid or liquid carriers. Those compositions contain a pesticidally effective amount of said compound or compounds, which amount may vary depending upon the particular compound, target pest, and method of use.

In general, the formulations comprise of from 0.01 to 95% by weight, preferably from 0.1 to 90% by weight, of the active ingredient. The active ingredients are employed in a purity of from 90% to 100%, preferably 95% to 100% (according to NMR spectrum).

The following are examples of formulations.

1. Products for dilution with water. For seed treatment purposes, such products may be applied to the seed diluted or undiluted:

A Soluble Concentrates (SL,LS)

10 parts by weight of a compound according to the invention are dissolved in water or in a water-soluble solvent. As an alternative, wetters or other auxiliaries are added. The active ingredient dissolves upon dilution with water.

B Dispersible Concentrates (DC)

20 parts by weight of a compound according to the invention are dissolved in cyclohexanone with addition of a dispersant, for example polyvinylpyrrolidone. Dilution with water gives a dispersion.

C Emulsifiable Concentrates (EC)

15 parts by weight of a compound according to the invention are dissolved in xylene with addition of calcium dodecylbenzenesulfonate and castor oil ethoxylate (in each case 5% strength). Dilution with water gives an emulsion.

D Emulsions (EW, EO; ES)

40 parts by weight of a compound according to the invention are dissolved in xylene with addition of calcium dodecylbenzenesulfonate and castor oil ethoxylate (in each case 5% strength). This mixture is introduced into water by means of an emulsifier (Ultraturrax) and made into a homogeneous emulsion. Dilution with water gives an emulsion.

E Suspensions (SC, OD, FS)

In an agitated ball mill, 20 parts by weight of a compound according to the invention are milled with addition of dispersant, wetters and water or an organic solvent to give a fine active ingredient suspension. Dilution with water gives a stable suspension of the active ingredient.

F Water-Dispersible Granules and Water-Soluble Granules (WG, SG)

50 parts by weight of a compound according to the invention are ground finely with addition of dispersants and wetters and made into water-dispersible or water-soluble granules by means of technical appliances (for example extrusion, spray tower, fluidized bed). Dilution with water gives a stable dispersion or solution of the active ingredient.

G Water-Dispersible Powders and Water-Soluble Powders (WP, SP,SS, WS)

75 parts by weight of a compound according to the invention are ground in a rotorstator mill with addition of dispersant, wetters and silica gel. Dilution with water gives a stable dispersion or solution with the active ingredient.

H Gel-Formulation (GF) (for Seed Treatment Purposes Only)

In an agitated ball mill, 20 parts by weight of the active compound(s) are comminuted with addition of 10 parts by weight of dispersants, 1 part by weight of a gelling agent wetters and 70 parts by weight of water or of an organic solvent to give a fine active compound(s) suspension. Dilution with water gives a stable suspension of the active compound(s), whereby a formulation with 20% (w/w) of active compound(s) is obtained.

2. Products to be applied undiluted. For seed treatment purposes, such products may be applied to the seed diluted:

I Dustable Powders (DP,DS)

5 parts by weight of a compound according to the invention are ground finely and mixed intimately with 95% of finely divided kaolin. This gives a dustable product.

J Granules (GR, FG, GG, MG)

0.5 parts by weight of a compound according to the invention is ground finely and associated with 95.5% carriers. Current methods are extrusion, spray drying or the fluidized bed. This gives granules to be applied undiluted.

K ULV Solutions (UL)

10 parts by weight of a compound according to the invention are dissolved in an organic solvent, for example xylene. This gives a product to be applied undiluted.

The active ingredients can be used as such, in the form of their formulations or the use forms prepared therefrom, e.g. in the form of directly sprayable solutions, powders, suspensions or dispersions, emulsions, oil dispersions, pastes, dusts, materials for spreading, or granules, by means of spraying, atomizing, dusting, scattering or pouring. The use forms depend entirely on the intended purposes; in any case, this is intended to guarantee the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within substantial ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even the active ingredient without additives.

Various types of oils, wetters, adjuvants, herbicides, fungicides, other pesticides, or bactericides may be added to the active ingredients, if appropriate just immediately prior to use (tank mix). These agents usually are admixed with the agents according to the invention in a weight ratio of 1:10 to 10:1.

The compounds of formula I are effective through both contact (via soil, glass, wall, bed net, carpet, plant parts or animal parts), and ingestion (bait, or plant part).

Specific Formulations

For use against ants, termites, wasps, flies, mosquitos, crickets, or cockroaches, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

Formulations of compounds of formula I as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

The compounds of formula I and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-diethyl-meta-toluamide (DEET), N,N-diethylphenylacetamide (DEPA), 1-(3-cyclohexan-1-yl-carbonyl)-2-methylpiperine, (2-hydroxymethyl-cyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is mostly done by dipping the textile material into emulsions or dispersions of the insecticide or spraying them onto the nets.

Seed Treatment

The compounds of formula I are also suitable for the treatment of seeds. Conventional seed treatments include for example flowable concentrates, solutions, powders for dry treatment, water dispersible powders for slurry treatment, water soluble powders and emulsion. Application to the seeds is carried out before sowing, either directly on the seeds or after having pregerminated the latter.

Seed Treatment formulations may comprise binders and optionally colorants.

Binders can be added to improve the adhesion of the active materials on the seeds after treatment. Suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers. Example of a gelling agent is carrageen (Satiagel®).

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Conventional seed treatment formulations include for example flowable concentrates FS, solutions LS, powders for dry treatment DS, water dispersible powders for slurry treatment WS, water-soluble powders SS and emulsion ES and EC. Application to the seeds is carried out before sowing, either directly on the seeds or after having pregerminated the latter.

In a preferred embodiment, a FS formulation is used. Typically, a FS formulation may comprise 1-800 g/l of active ingredient, 1-200 g/l Surfactant, 0 to 200 g/l anti-freezing agent, 0 to 400 g/l of binder, 0 to 15 g/l of a pigment and up to 1 liter of a solvent, preferably water.

For seed treatment purposes, respective seed treatment formulations can be diluted 2-10 fold leading to concentrations in the ready to use preparations of 0.01 to 60% by weight active compound by weight, preferably 0.1 to 40% by weight.

The application rates vary with the crops. In the treatment of seed, the application rates of the compounds of formula I are generally from 0.1 g to 10 kg of compounds of formula I per 100 kg of seeds, desirably 0.25 kg of compounds of formula I per 100 kg of seeds. In general, rates from 1 g to 5 kg compounds of formula I per 100 kg of seeds, more desirably from 1 g to 2.5 kg per 100 kg of seeds are suitable. For specific crops such as lettuce the rates can be higher.

In the control of pests, the application of the compound of formula I or of the composition comprising it is carried out by spraying or dusting the seeds or the soil (and thereby the seeds) after sowing, wherein treating the seeds prior to sowing is preferred.

A further subject of the invention is a method of treating the seed in the seed drill with a granular formulation containing the active ingredient or a composition comprising it, with optionally one or more solid or liquid, agriculturally acceptable carriers and/or optionally with one or more agriculturally acceptable surfactants. This method is advantageously employed in seedbeds of cereal, maize, cotton and sunflower.

For cereals and maize, the rates for compounds of formula I are between 50 and 1000 g/ha.

The invention also relates to the seeds, and especially the true seed comprising, that is, coated with and/or containing, a compound of formula I or a composition comprising it. The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

The seed comprises the inventive mixtures in an amount of from 0.1 g to 100 kg per 100 kg of seed.

Mixing Partners

Compositions to be used according to this invention may also contain other active ingredients, for example other pesticides, insecticides, herbicides, fungicides, other pesticides, or bactericides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

The following list of pesticides together with which the compounds of formula I can be used, is intended to illustrate the possible combinations, but not to impose any limitation:

Organophosphates: Acephate, Azinphos-methyl, Chlorpyrifos, Chlorfenvinphos, Diazinon, Dichlorvos, Dicrotophos, Dimethoate, Disulfoton, Ethion, Fenitrothion, Fenthion, Isoxathion, Malathion, Methamidophos, Methidathion, Methyl-Parathion, Mevinphos, Monocrotophos, Oxydemeton-methyl, Paraoxon, Parathion, Phenthoate, Phosalone, Phosmet, Phosphamidon, Phorate, Phoxim, Pirimiphos-methyl, Profenofos, Prothiofos, Sulprophos, Triazophos, Trichlorfon;

Carbamates: Alanycarb, Benfuracarb, Carbaryl, Carbosulfan, Fenoxycarb, Furathiocarb, Indoxacarb, Methiocarb, Methomyl, Oxamyl, Pirimicarb, Propoxur, Thiodicarb, Triazamate;

Pyrethroids: Bifenthrin, Cyfluthrin, Cypermethrin, Deltamethrin, Esfenvalerate, Ethofenprox, Fenpropathrin, Fenvalerate, Cyhalothrin, Lambda-Cyhalothrin, Permethrin, Silafluofen, Tau-Fluvalinate, Tefluthrin, Tralomethrin, Zeta-Cypermethrin;

Arthropod growth regulators: a) chitin synthesis inhibitors: benzoylureas: Chlorfluazuron, Diflubenzuron, Flucycloxuron, Flufenoxuron, Hexaflumuron, Lufenuron, Novaluron, Teflubenzuron, Triflumuron; Buprofezin, Diofenolan, Hexythiazox, Etoxazole, Clofentazine; b) ecdysone antagonists: Halofenozide, Methoxyfenozide, Tebufenozide; c) juvenoids: Pyriproxyfen, Methoprene, Fenoxycarb; d) lipid biosynthesis inhibitors: Spirodiclofen;

Various: Abamectin, Acequinocyl, Amitraz, Azadirachtin, Bifenazate, Cartap, Chlorfenapyr, Chlordimeform, Cyromazine, Diafenthiuron, Dinetofuran, Diofenolan, Emamectin, Endosulfan, Ethiprole, Fenazaquin, Fipronil, Formetanate, Formetanate hydrochloride, Hydramethylnon, Imidacloprid, Indoxacarb, 4-{(-{(2Z)-2-({[4-(trifluoromethoxy)anilino]carbonyl}hydrazono)-2-[3-(trifluoromethyl)-phenyl]ethyl}benzonitrile), Nitenpyram, Pymetrozine, Pyridaben, Pyridalyl, Spinosad, Spirodiclofen, Spiromesifen, Sulfur, Tebufenpyrad, Thiamethoxam, and Thiocyclam.

Fungicides are those selected from the group consisting of acylalanines such as benalaxyl, metalaxyl, ofurace, oxadixyl, amine derivatives such as aldimorph, dodine, dodemorph, fenpropimorph, fenpropidin, guazatine, iminoctadine, spiroxamin, tridemorph anilinopyrimidines such as pyrimethanil, mepanipyrim or cyrodinyl, antibiotics such as cycloheximid, griseofulvin, kasugamycin, natamycin, polyoxin or streptomycin, azoles such as bitertanol, bromoconazole, cyproconazole, difenoconazole, dinitroconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol, dicarboximides such as iprodion, myclozolin, procymidon, vinclozolin, dithiocarbamates such as ferbam, nabam, maneb, mancozeb, metam, metiram, propineb, polycarbamate, thiram, ziram, zineb, heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine, copper fungicides such as Bordeaux mixture, copper acetate, copper oxychloride, basic copper sulfate, nitrophenyl derivatives such as binapacryl, dinocap, dinobuton, nitrophthalisopropyl phenylpyrroles such as fenpiclonil or fludioxonil, sulfur, other fungicides such as acibenzolar-S-methyl, benthiavalicarb, carpropamid, chlorothalonil, cyflufenamid, cymoxanil, dazomet, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid, strobilurins such as azoxystrobin, dimoxystrobin, fluoxastrobin, kresoxim-methyl, metominostrobin, orysastrobin, picoxystrobin or trifloxystrobin, sulfenic acid derivatives such as captafol, captan, dichlofluanid, folpet, tolylfluanid, cinnemamides and analogs such as dimethomorph, flumetover or flumorph.

Application Methods

The insects may be controlled by contacting the target parasite/pest, its food supply, habitat, breeding ground or its locus with a pesticidally effective amount of compounds of or compositions of formula I.

"Locus" means a habitat, breeding ground, plant, seed, soil, area, material or environment in which a pest or parasite is growing or may grow.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds of formula I and its compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of the invention can also be applied preventively to places at which occurrence of the pests is expected.

The compounds of formula I may be also used to protect growing plants from attack or infestation by pests by contacting the plant with a pesticidally effective amount of compounds of formula I. As such, "contacting" includes both direct contact (applying the compounds/compositions directly on the pest and/or plant—typically to the foliage, stem or roots of the plant) and indirect contact (applying the compounds/compositions to the locus of the pest and/or plant).

Application Rates

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in bait compositions, the typical content of active ingredient is from 0.001 weight % to 15 weight %, desirably from 0.001 weight % to 5% weight % of active compound.

For use in spray compositions, the content of active ingredient is from 0.001 to 80 weights %, preferably from 0.01 to 50 weight % and most preferably from 0.01 to 15 weight %.

For use in treating crop plants, the rate of application of the active ingredients of this invention may be in the range of 0.1 g to 4000 g per hectare, desirably from 25 g to 600 g per hectare, more desirably from 50 g to 500 g per hectare.

In the treatment of seed, the application rates of the mixture are generally from 0.1 g to 10 kg per 100 kg of seed, preferably from 1 g to 5 kg per 100 kg of seed, in particular from 1 g to 200 g per 100 kg of seed.

The present invention is now illustrated in further detail by the following examples.

I. SYNTHESIS EXAMPLES

Example 1

N,N-Dimethyl-2-cyano-3-difluoromethoxyphenyl-sulfonamide (Compound No. 1)

Synthesis Route 1

1.1: 2-Methyl-1-nitro-3-propylsulfanylbenzene 400 g (2.63 mol) of 2-methyl-3-nitroaniline, 655 g (4.35 mol) of dipropyl disulfide, 30 g (0.47 mol) of copper powder were suspended in 1000 ml of chloroform and heated to 70 to 75° C. Then, over the course of 70 min, 339 g (3.28 mol) of n-butyl nitrite were added dropwise. The mixture was stirred at 75 to 80° C. for 4 h. The reaction mixture was cooled to room temperature and then washed three times with 1000 ml of concentrated hydrochloric acid, twice with 20% strength aqueous sodium hydroxide solution and once with saturated sodium chloride solution. After drying over magnesium sulfate, the solvent was distilled off in vacuo. The result was a dark oil which was purified by vacuum distillation (b.p. 127° C./1.2 mbar). Yield: 267 g (48% of theory) of the desired product.

$^1$H NMR (in CDCl$_3$): δ=1.05 ppm (t, 3H, aliph. Me), 1.7 ppm (m, 2H, aliph. CH$_2$), 2.9 ppm (t, 2H, S CH$_2$), 7.3 ppm (m, 1H, arom. H), 7.45 ppm (d, 1H, arom. H), 7.5 ppm (d, 1H, arom. H).

1.2: 2-Hydroxy-6-propylsulfanylbenzonitrile 30 g (0.14 mol) of 2-methyl-1-nitro-3-propylsulfanylbenzene, 18.9 g (0.18 mol) of n-butyl nitrite were dissolved in 120 ml of dimethylformamide and cooled to (−20)° C. Then a solution of potassium t-butoxide in 120 ml of DMF is added dropwise over the course of 25 min. After the reaction mixture had been stirred at (−25)° C. for one hour, it was stirred into a mixture of ice and 150 ml of concentrated hydrochloric acid. The mixture was warmed to room temperature, and the resulting solid was filtered off with suction and washed several times with water and once with cyclohexane. The solid was purified by stirring with a little amount of methylene chloride. Yield: 12.4 g (46% of theory) of the desired product.

$^1$H NMR (in CDCl$_3$): δ=1.05 ppm (t, 3H, aliph. Me), 1.7 ppm (m, 2H, aliph. CH$_2$), 3.0 ppm (t, 2H, S CH$_2$), 6.8 ppm (d, 1H, arom. H), 6.9 ppm (d, 1H, arom. H), 7.35 ppm (m, 1H, arom. H).

1.3: 2-Difluoromethoxy-6-propylsulfanylbenzonitrile 10.8 g (56 mmol) of 2-hydroxy-6-propylsulfanylbenzonitrile were dissolved in 120 ml of dimethylformamide, and 15.5 g (0.11 mol) of anhydrous potassium carbonate were added. Then, at room temperature, 8.2 g of bromodifluoromethane were passed in, and the mixture was stirred at room temperature for 5 hours. Then 15.5 g (0.11 mol) of anhydrous potassium carbonate and 7.2 g of bromodifluoromethane were added, and the mixture was stirred at room temperature overnight. The reaction mixture was worked up by pouring into water and extracting twice with methyl tert.-butyl ether. The organic phase was separated, washed several times with water and concentrated. The solid has been dried in vacuo at 50° C. Yield: 12.3 g of an oily residue.

Synthesis Route 2

1.5: 2-Fluoro-6-methoxybenzonitrile (Analogous to WO 99/14187)

640.5 g (4.6 mol) of difluorobenzonitrile were dissolved in 3.5 l of methanol and then cooled to 0-5° C. 828.8 g of 30% strength sodium methoxide solution were added dropwise in this temperature range, and the reaction mixture was stirred at room temperature overnight. Then the reaction mixture was added to 20 l of water and the precipitate was filtered off with suction and washed twice with water and twice with heptane. The solid was dried in vacuo at 50° C. Yield: 740 g (99% of theory) of a white solid with a purity of >95% according to GC.

$^1$H NMR (in CDCl$_3$): δ=3.95 ppm (s, 3H, O—CH$_3$), 6.85 ppm (m, 2H, arom. H), 7.5 ppm (q, 1H, arom. H).

1.6: 2-Fluoro-6-hydroxybenzonitrile (analogous to WO 99/14187)

151 g (1 mol) of 2-fluoro-6-methoxybenzonitrile and 346.5 g (3 mol) of pyridinium hydrochloride were introduced into a 2 l flask and then slowly heated to 190° C. under a protective gas atmosphere and then stirred at this temperature for 5 h. The mixture was cooled by slowly stirring to room temperature overnight. Then 1000 ml of water were added, and the mixture was heated to 80° C. After adding 1000 ml of methyl tert.-butyl ether, the phases were separated and the aqueous phase was back-extracted twice with 500 ml of methyl tert.-butyl ether. The combined methyl tert.-butyl ether phases were washed once with 800 ml of 10% strength aqueous sodium hydroxide solution and once with 400 ml of water. The two aqueous phases were combined, adjusted to pH 2 with concentrated hydrochloric acid and washed three times with 500 ml of methylene chloride. Then, the combined organic phases were washed once with 10% strength hydrochloric acid. The organic phase was dried over sodium sulfate. Finally, the solvent was distilled off in vacuo. Yield: 120 g (87% of theory) of the desired product of purity >99% according to GC.

$^1$H NMR (in D$_6$ dimethylsulfoxide): δ=6.85 ppm (m, 2H, arom. H), 7.55 ppm (q, 1H, arom. H), 11.7 ppm (s, 1H, OH).

1.7: 2-Difluoromethoxy-6-fluorobenzonitrile 150 g (1.1 mol) of 2-fluoro-6-hydroxybenzonitrile were introduced into 2000 ml of ethylene glycol dimethyl ether. Then, 262.8 g (3.3 mol) of concentrated NaOH were added dropwise. The reaction mixture was heated to 65° C. and 95 g (1.1 mol) of chlorodifluoromethane were passed in. The mixture was stirred at 65° C. for one hour and at room temperature overnight. Then, the reaction mixture was stirred into 3 l of water, followed by extraction repeated three times with a total of 800 ml of methyl tert.-butyl ether. The combined organic phases were washed twice with 500 ml of water, once with 250 ml of sodium chloride solution and dried over sodium sulfate. Finally, the solvent was distilled off in vacuo. Yield: 211 g (99% of theory) of the desired product with a purity of 97% according to GC.

$^1$H NMR (in CDCl$_3$): δ=6.5-6.9 ppm (t, 1H, OCF$_2$H), 7.15 ppm (m, 2H, arom. H), 7.65 ppm (m, 1H, arom. H).

1.8: 2-Difluoromethoxy-6-propylsulfanylbenzonitrile 180 g (0.96 mol) 2-difluoromethoxy-6-fluorobenzonitrile were introduced into 1.5 l of dimethylformamide at room temperature. 73.2 g (0.96 mol) of propanethiol were added dropwise and, after cooling to 0° C., 70 g (1.25 mol) of potassium hydroxide pellets, dissolved in 600 ml of water, were added dropwise at 0° C. The mixture was stirred for one hour and then warmed to room temperature. The reaction mixture was stirred into 3.5 l of ice-water and extracted three times with 500 ml of methyl tert.-butyl ether. The combined organic phases were washed twice with 500 ml of 1N hydrochloric acid and dried over sodium sulfate. Then, the solvent was distilled off in vacuo. The oil obtained was distilled in vacuo (b.p.: 180-185° C./0.5 mbar). Yield: 76% of theory.

$^1$H NMR (in CDCl$_3$): δ=1.1 ppm (t, 3H, CH$_3$), 1.75 ppm (m, 2H, CH$_2$CH$_3$), 3.0 ppm (t, 2H, SCH$_2$), 6.5-6.85 ppm (t, 1H, OCF$_2$H), 7.05 ppm (d, 1H, arom. H), 7.2 ppm (d, 1H, arom. H), 7.5 ppm (t, 1H, arom. H).

1.9: 2-Cyano-3-difluoromethoxyphenylsulfonyl Chloride

A mixture of 100 ml of chlorobenzene and 20 ml of water was cooled to 10° C. and pre-saturated with gaseous chlorine. A solution of 20 g (0.08 mol) of 2-difluoromethoxy-6-propylsulfanylbenzonitrile in 200 ml of chlorobenzene was added dropwise while passing chlorine through the solution. After 2 hours of stirring the conversion was complete. The mixture was cooled to 0-5° C., dried over sodium sulfate and evaporated. The oily residue (27.8 g) contained by-products formed from chlorobenzene but was used without further purification for the next step. If necessary, the sulfonyl chloride could have been purified by column chromatography using cyclohexane and toluene as eluents.

$^1$H NMR (in CDCl$_3$): δ [ppm]=6.80 (t, 1H), 7.79 (d, 1H), 7.89 (t, 1H), 8.10 (d, 1H).

1.10. N,N-Dimethyl-2-cyano-3-difluoromethoxyphenylsulfonamide

To a solution of 0.65 g (2.4 mmol) of purified 2-cyano-3-difluoromethoxyphenylsulfonyl chloride in 20 ml of tetrahydrofuran a solution of 274 mg (2.4 mmol) of dimethylamine and 510 mg of sodium carbonate in 15 ml of water was added at room temperature. The reaction mixture was stirred at room temperature for 5 minutes before water was added. The aqueous phase was acidified to pH=1 using hydrochloric acid (10% strength by weight, aqueous solution). The aqueous phase was then extracted three times with dichloromethane. The combined organic extracts were dried over sodium sulfate and filtered. The filtrate was concentrated in vacuo and the resulting residue was triturated with methyl tert-butyl ether. Yield: 0.53 g (79% of theory) of the title compound having a melting point of 100-102° C.

Example 2

N,N-Dimethyl-2-cyano-3-methoxyphenylsulfonamide (Compound No. 2)

2.1: 2-Amino-6-methoxybenzonitrile

A solution of 70 g (0.5 mol) of 2-amino-6-fluorobenzonitrile (prepared, e.g. according to U.S. Pat. No. 4,504,660) in 250 ml of N,N-dimethylformamide was prepared, and a solution of 30.6 g (0.55 mol) of sodium methoxide in 70 ml of methanol was added dropwise at room temperature while stirring. The mixture was then refluxed for 5 hours with stirring. The completion of the reaction was monitored by TLC. An additional 25 g of sodium methoxide in 35 ml methanol were added and the reaction mixture was refluxed for an additional 4 hours while stirring. The reaction mixture was concentrated under reduced pressure. The resulting residue was triturated with water, filtered off with suction and the solids obtained were dissolved in ethyl acetate. The resulting solution was concentrated in vacuo. The obtained residue was triturated with petroleum ether and filtered off with suction. Yield: 48 g (63% of theory) of a brownish solid having a melting point of 143-146° C.

2.2: 2-Cyano-3-methoxyphenylsulfonyl Chloride 10 g of concentrated hydrochloric acid were slowly added to a solution of 4.0 g (27 mmol) of 2-amino-6-methoxybenzonitrile in 32 ml of glacial acetic acid at room temperature while stirring. The mixture was stirred at room temperature for 10 minutes. Then, a solution of 1.9 g (27.3 mmol) of sodium nitrite in 5 ml of water was added at 5-10° C. and the reaction mixture was stirred at 0° C. for 1 hour to obtain the diazonium salt. In a separate flask, a saturated solution of sulfur dioxide in 68 ml of glacial acetic acid was prepared at room temperature and a solution of 1.7 g of copper(II) chloride in 4 ml of water was added. The reaction mixture of the diazonium salt which had been prepared beforehand was then quickly added to the solution of the copper salt. The resulting mixture was stirred at room temperature for an additional 2.5 hours. The reaction mixture was then poured into ice-cooled water. The aqueous layer was extracted three times with dichloromethane. The combined organic extracts were dried over a drying agent and filtered off with suction. The filtrate was concentrated in vacuo. Yield: 5.3 g (85% of theory) of the title compound having a melting point of 96-99° C.

2.3:
N,N-Dimethyl-2-cyano-3-methoxyphenylsulfonamide

A solution of 1.25 g (5.4 mmol) of 2-cyano-3-methoxyphenylsulfonyl chloride in 30 ml of tetrahydrofuran was added to a solution of 960 mg (12 mmol) of an aqueous solution of methylamine (40% by weight) in 20 ml of tetrahydrofuran at room temperature. The reaction mixture was stirred at room temperature for 30 minutes before water was added. The aqueous phase was acidified to pH=3 using hydrochloric acid (10% strength by weight, aqueous solution). The aqueous phase was then extracted three times with dichloromethane. The combined organic extracts were dried over sodium sulfate and filtered. The filtrate was concentrated in vacuo and the resulting residue was triturated with methyl tert.-butyl ether. Yield: 0.28 g (23% of theory) of the title compound having a melting point of 121-128° C.

The compounds no. 3 to 9 listed in the following table 1 were prepared analogously.

TABLE 1

(Structure: benzene ring with Alk at top, $R^3$ at position, CN, $SO_2$-N($R^1$)($R^2$), $R^5$, H; $R^4$ = H)

| Example | $R^1$ | $R^2$ | Alk | $R^3$ | $R^5$ | m.p. [° C.]*/ $^1$H-NMR**/ LC/MS*** |
|---|---|---|---|---|---|---|
| No. 3 | $C_2H_5$ | $C_2H_5$ | $OCH_3$ | H | H | 77-83 |
| No. 4 | $CH_2CH=CH_2$ | $CH_2CH=CH_2$ | $OCH_3$ | H | H | 60-73 |
| No. 5 | $CH_3$ | $CH_3$ | $OCH_3$ | Br | H | 75-80 |
| No. 6 | $CH_3$ | $CH_3$ | $OCH_3$ | H | $NO_2$ | Oil |
| No. 7 | $CH_3$ | $C_2H_5$ | $OCHF_2$ | H | H | Oil |
| No. 8 | $CH_3$ | $CH_3$ | $OCH_3$ | H | $NH_2$ | Oil |
| No. 9 | $C_2H_5$ | $C_2H_5$ | $OCHF_2$ | H | H | Oil |
| No. 10 | $CH_3$ | $CH_3$ | $OC_2H_5$ | H | H | 86-94 |
| No. 11 | $C_2H_5$ | $C_2H_5$ | $OC_2H_5$ | H | H | Oil |
| No. 12 | $CH_3$ | $CH_3$ | $OCH(CH_3)_2$ | H | H | Oil |
| No. 13 | $CH_3$ | $CH_3$ | $OCH_2CHClCH_2Cl$ | H | H | Oil |
| No. 14 | $CH_3$ | $CH_3$ | $OCF_2$—Cl | H | H | 83-85 |
| No. 15 | $CH_3$ | $CH_3$ | $OCF_3$ | H | H | 95-98 |
| No. 16 | $CH_3$ | $C_2H_5$ | $OCF_3$ | H | H | Oil |
| No. 17 | $C_2H_5$ | $C_2H_5$ | $OCF_3$ | H | H | Oil |
| No. 18 | $CH_3$ | $C_2H_5$ | $OCF_2Cl$ | H | H | Oil |
| No. 19 | $C_2H_5$ | $C_2H_5$ | $OCF_2Cl$ | H | H | Oil |
| No. 20 | $CH_3$ | $CH_3$ | $OCH_3$ | H | CH3 | 89-93 |
| No. 21 | $CH_3$ | $CH_3$ | $OCH_3$ | H | $C_2H_5$ | 138-140 |
| No. 22 | $CH_3$ | $CH_3$ | $OCH_3$ | H | $CH_3OCO$ | 134-138 |
| No. 23 | $CH_3$ | $CH_3$ | $OCH_3$ | H | Cl | LC/MS*** |
| No. 24 | $CH_3$ | $CH_3$ | $OCH_3$ | H | H | $^1$H-NMR** |
| No. 25 | $CH_3$ | $C_2H_5$ | $OCF_2$—CHFCl | H | H | $^1$H-NMR |
| No. 26 | $CH_3$ | $CH_3$ | $OCH_3$ | H | F | 123-125 |
| No. 27 | $CH_3$ | $C_2H_5$ | $OCH_3$ | H | F | $^1$H-NMR** |
| No. 28 | $CH_3$ | $CH(CH_3)_2$ | $OCH_3$ | H | F | $^1$H-NMR** |
| No. 29 | $CH_3$ | $CH_2C=CH$ | $OCH_3$ | H | F | $^1$H-NMR** |
| No. 30 | $CH_3$ | $CH_3$ | $OCH_3$ | $OCH_3$ | H | $^1$H-NMR** |
| No. 31 | $CH_3$ | $CH_3$ | $OCHF_2$ | H | F | 102-105 |

TABLE 1-continued

[Structure: benzene ring with Alk at top, R³ and H on left, R⁵ at bottom, CN and SO₂-N(R¹)(R²) on right, labeled I (R⁴ = H)]

| Example | R¹ | R² | Alk | R³ | R⁵ | m.p. [° C.]*/ $^1$H-NMR** LC/MS*** |
|---|---|---|---|---|---|---|
| No. 32 | CH₃ | CH₃ | OCH₃ | Cl | Br | 93-98 |
| No. 33 | CH₃ | CH₃ | OCH₃ | F | H | $^1$H-NMR** |

*m.p. = melting point
**$^1$H-NMR see table 2
**LC/MS see table 2

TABLE 2

$^1$H-NMR or LC/MS

| | |
|---|---|
| No. 23 | LC/MS $R_T$ = 2.59 min, [M + H]⁺ 275/277 |
| No. 24 | $^1$H-NMR [CDCl₃]: δ in ppm: 2.40 (3H, s), 2.90 (6H, s), 4.01 (3H, s) 7.55 (1H, d), 7.70 (1H, d) |
| No. 25 | $^1$H-NMR [CDCl₃]: δ in ppm: 1.20 (3H, t), 2.94 (3H, s), 3.35 (2H, q), 6.43 (1H, m), 7.67 (1H, d), 7.80 (1H, t), 8.01 (1H, d) |
| No. 27 | $^1$H-NMR [CDCl₃]: δ in ppm: 1.18 (3H, t), 2.95 (3H, s), 3.36 (2H, q), 3.99 (3H, s), 7.20 (1H, m), 7.42 (1H, t) |
| No. 28 | $^1$H-NMR [CDCl₃]: δ in ppm: 1.05 (3H, d), 2.89 (3H, s), 3.99 (3H, s), 4.32 (1H, m), 7.15 (1H, m), 7.40 (1H, t) |
| No. 29 | $^1$H-NMR [CDCl₃]: δ in ppm: 2.11 (1H, m), 3.02 (3H, s), 4.00 (3H, s), 4.20 (2H, s), 7.19 (1H, m), 7.41 (1H, t) |
| No. 30 | $^1$H-NMR [CDCl₃]: δ in ppm: 2.85 (6H, s), 4.00 (3H, s), 4.06 (3H, s), 7.16 (1H, d), 7.72 (1H, d) |
| No. 33 | $^1$H-NMR [CDCl₃]: δ in ppm: 2.90 (6H, s), 4.19 (3H, s), 7.41 (1H, t), 7.70 (1H,m) |

II. EXAMPLES OF ACTION AGAINST PESTS

The action of the compounds of the formula I against pests was demonstrated by the following experiments.

Nematicidal Evaluation

Test compounds were prepared and formulated into aqueous formulations using acetone. The formulations were tested using root knot nematode (2nd instar) and soybean cyst nematode (2nd instar) as target species.

Test Procedures for Root-Knot Nematode (*Meloidogyne incognita*):

Tomato plants (var. Bonny Best) were grown in the greenhouse in plastic tubs (4 to 6 plants per tub). The plants and soil (a 50:50 mixture of sand and "New Egypt" sandy loam) were infested with *M. incognita* J2 (to establish the "in-house" colony, *M. incognita* J2 were initially acquired from Auburn University). The plants were kept pruned and were used on an "as needed" basis. The tomato plants were kept in the cylinder containing hydroponic solution and aerated until the nematodes were no longer present in the solution (usually about 60 days). The cultures were checked daily by eluting a small volume (approximately 20 ml) from the bottom of a funnel attached to the cylinder into a small crystallizing dish and observed using a binocular dissecting scope. If needed for testing, the nematodes were cleaned and concentrated by pouring the culture solution through a sieve for cleaning and a sieve for concentrating. The nematodes were then resuspended in water to a concentration of approximately 20 to 50 nematodes per 50 μl. These were counted by putting 25 μl of the nematode solution into a well of an unused well of an assay plate. The total was then multiplied by 2 for a final total of nematodes per 50 μl of solution. To microtiter plates containing about 1.0 mg of compound, 80:20 acetone was added to each well and the solution was mixed to obtain the desired compound concentration. The nematode solution was added to each plate. The plates were then sealed and they were placed in an incubator at 27° C. and 50% (+/−2%) relative humidity. After 72 hours, the population mortality was read, whereby immobility of nematodes was regarded as mortality.

Test Procedures for Soybean Cyst Nematode (*Heterodera glycine*):

The soybean bean cyst nematode culture was maintained in a greenhouse and soybean eggs and J2 larvae were obtained for testing by dislodging soybean cysts from the roots with a sieve. The cysts were broken to release the eggs and the eggs were maintained in water. The eggs hatched after 5-7 days at 28° C. To microtiter plates containing about 150 μg of compound, 80:20 acetone was added to each well and the solution was mixed to obtain the desired compound concentration. The nematode solution was added to the plate. The plates were then sealed and placed in an incubator at 27° C. and 50% (+/−2%) relative humidity. After 72 hours, the population mortality was read, whereby immobility of nematodes was regarded as mortality.

Activity Against Insects and Arachnids

Southern Armyworm (*Spodoptera eridania*), 2nd Instar Larvae

The active compounds were formulated for testing the activity against insects and arachnids as a 10.000 ppm solution in a mixture of 35% acetone and water, which was diluted with water, if needed.

A Sieva lima bean leaf expanded to 7-8 cm in length is dipped in the test solution with agitation for 3 seconds and allowed to dry in a hood. The leaf is then placed in a 100×10 mm petri dish containing a damp filter paper on the bottom and ten 2nd instar caterpillars. At 5 days, observations are made of mortality, reduced feeding, or any interference with normal molting.

Green Peach Aphid (*Myzus persicae*)

The active compounds were formulated in 50:50 acetone:water and 100 ppm Kinetic® surfactant.

Pepper plants in the $2^{nd}$ leaf-pair stage (variety 'California Wonder') were infested with approximately 40 laboratory-reared aphids by placing infested leaf sections on top of the test plants. The leaf sections were removed after 24 hr. The leaves of the intact plants were dipped into gradient solutions of the test compound and allowed to dry. Test plants were maintained under fluorescent light (24 hour photoperiod) at about 25° C. and 20-40% relative humidity. Aphid mortality on the treated plants, relative to mortality on check plants, was determined after 5 days.

In this test, compounds nos. 1, 2, 4, 5, 7, 9 and 10 at 300 ppm showed over 85% mortality in comparison with untreated controls.

Cotton Aphid (*Aphis gossypii*)

The active compounds were formulated in 50:50 acetone:water and 100 ppm Kinetic® surfactant.

Cotton plants in the cotyledon stage (variety 'Delta Pine', one plant per pot) were infested by placing a heavily infested leaf from the main colony on top of each cotyledons. The aphids were allowed to transfer to the host plant overnight, and the leaf used to transfer the aphids was removed. The cotyledons were dipped in the test solution and allowed to dry. After 5 days, mortality counts were made.

In this test, compounds nos. 1, 2, 4, 5, 7, 9, 10, 14 and 15 at 300 ppm showed over 85% mortality in comparison with untreated controls.

Bean Aphid (*Aphis fabae*)

The active compounds were formulated in 50:50 acetone:water and 100 ppm Kinetic® surfactant.

Nasturtium plants grown in Metro mix in the $1^{st}$ leaf-pair stage (variety 'Mixed Jewel') were infested with approximately 20-30 laboratory-reared aphids by placing infested cut plants on top of the test plants. The cut plants were removed after 24 hr. Each plant was dipped into the test solution to provide complete coverage of the foliage, stem, protruding seed surface and surrounding cube surface and allowed to dry in the fume hood. The treated plants were kept at about 25° C. with continuous fluorescent light. Aphid mortality is determined after 3 days.

In this test, compounds nos. 1, 2, 4, 5, 7, 9, 14 and 15 at 300 ppm showed over 85% mortality in comparison with untreated controls.

Silverleaf Whitefly (*Bemisia argentifolii*)

The active compounds were formulated in 50:50 acetone:water and 100 ppm Kinetic® surfactant.

Selected cotton plants were grown to the cotyledon state (one plant per pot). The cotyledons were dipped into the test solution to provide complete coverage of the foliage and placed in a well-vented area to dry. Each pot with treated seedling was placed in a plastic cup and 10 to 12 whitefly adults (approximately 3-5 day old) were introduced. The insects were collected using an aspirator and an 0.6 cm, non-toxic Tygon® tubing (R-3603) connected to a barrier pipette tip. The tip, containing the collected insects, was then gently inserted into the soil containing the treated plant, allowing insects to crawl out of the tip to reach the foliage for feeding. The cups were covered with a reusable screened lid (150 micron mesh polyester screen PeCap from Tetko Inc.). Test plants were maintained in the holding room at about 25° C. and 20-40% humidity for 3 days avoiding direct exposure to the fluorescent light (24 photoperiod) to prevent trapping of heat inside the cup. Mortality was assessed 3 days after treatment of the plants.

2-Spotted Spider Mite (*Tetranychus urticae*, OP-Resistant Strain)

The active compounds were formulated in 50:50 acetone:water and 100 ppm Kinetic® surfactant.

Sieva lima bean plants (variety 'Henderson') with primary leaves expanded to 7-12 cm were infested by placing on each a small piece from an infested leaf (with about 100 mites) taken from the main colony. This was done at about 2 hours before treatment to allow the mites to move over to the test plant to lay eggs. The piece of leaf used to transfer the mites was removed. The newly-infested plants were dipped in the test solution and allowed to dry. The test plants were kept under fluorescent light (24 hour photoperiod) at about 25° C. and 20-40% relative humidity. After 5 days, one leaf was removed and mortality counts were made.

Activity Against Non-Crop Pests

Yellowfever Mosquitos (*Aedes aegypti*)

The test compound (1 Vol % in acetone) was applied to water in glass dishes containing 4th instar aedes aegypti. The test dishes were maintained at about 25° C. and observed daily for mortality. Each test weas replicated in 3 test dishes.

Eastern Subterranean Termites (*Reticulitérmes flávipes*)

Toxicant treatments (1.0% test compound w/w) were applied to 4.25 cm (diam.) filter papers (VWR #413, qualitative) in acetone solution. Treatment levels (% test compound) were calculated on basis of a mean weight per filter paper of 106.5 mg. Treatment solutions were adjusted to provide the quantity of toxicant (mg) required per paper in 213 ml of acetone (volume required for saturation of paper). Acetone only was applied for untreated controls. Treated papers were vented to evaporate the acetone, moistened with 0.25 ml water, and enclosed in 50×9 mm Petri dishes with tight-fit lids (3-mm hole in side of each dish for termite entry).

Termite bioassays were conducted in 100×15 mm Petri dishes with 10 g fine sand spread in a thin layer over the bottom of each dish. An additional 2.5 g sand was piled against the side of each dish. The sand was moistened with 2.8 ml water applied to the piled sand. Water was added to dishes as needed over the course of the bioassays to maintain high moisture content. Bioassays were done with one treated filter (inside enclosure) and 30 termite workers per test dish. Each treatment level was replicated in 2 test dishes. Test dishes were maintained at about 25° C. and 85% humidity for 12 days and observed daily for mortality.

Orchid Thrips (*Dichromothrips corbetti*)

*Dichromothrips corbetti* adults used for bioassay were obtained from a colony maintained continuously under laboratory conditions. For testing purposes, the test compound was diluted to a concentration of 500 ppm (wt compound: vol diluent) in a 1:1 mixture of acetone:water, plus 0.01% Kinetic surfactant.

Thrips potency of each compound was evaluated by using a floral-immersion technique. Plastic petri dishes were used as test arenas. All petals of individual, intact orchid flowers were dipped into treatment solution for approximately 3 seconds and allowed to dry for 2 hours. Treated flowers were placed into individual petri dishes along with 10-15 adult thrips. The petri dishes were then covered with lids. All test arenas were held under continuous light and a temperature of about 28° C. for duration of the assay. After 4 days, the numbers of live thrips were counted on each flower, and along inner walls of each petri dish. The level of thrips mortality was extrapolated from pre-treatment thrips numbers.

Seed Treatment

Experimental compound no. 1 (N,N-Dimethyl-2-cyano-3-difluoromethoxyphenylsulfonamide) was evaluated to determine their insecticidal efficacy for control of foliar aphids when applied as seed treatment.

Compound Preparation

Experimental compound no. 1 was formulated by dissolving 10.5 mg technical material in 45 μl acetone then adding 255 μl 0.05% aqueous TWEEN 20 (polyoxyethylene (20) sorbitan monolaurate).

Cotton Seed Treatment

Twenty-five cotton seeds (variety Sure-Grow 747) were placed in a 20-ml glass vial and then 150 μl of the compound formulation were pipetted onto the side of the vial just above the seeds. Vials were vortexed for 30 seconds to rapidly spin the seeds within the vial to apply the compound to the seeds. Treated seeds were then air-dried. Solvent blank controls are created by treating seeds with a 15% acetone/0.05% aqueous TWEEN 20 solution.

Insecticide Efficacy Evaluation

Twenty-four cotton seeds were planted in Metro Mix potting mix in twelve 7.6-cm-square pots, 2 seeds per pot. Crop selectivity was determined by comparing seedling emergence and recording any foliar and shoot symptoms.

Seedling plants were thinned to one plant per pot. At the cotyledon stage 6 plants per treatment were infested with cotton aphids (*Aphis gossypii*) by manually transferring circa 25 aphids to each plant on a piece of leaf tissue cut from a donor plant that was infested with aphids. The exact number of aphids transferred to each plant was recorded.

Four days after infestation, live aphids on each plant were counted. The aphid population increase for each control plant was calculated by dividing the final aphid population by the initial population. The median aphid population increase on the solvent blank controls was then calculated. This median aphid population increase was used to determine the expected final aphid population expected on each treated plant by multiplying the initial aphid population on the treated plant by the median aphid population increase of the solvent blank controls.

Compound no. 1 showed significant reduction of the aphid population.

We claim:

1. A process for the preparation of a 2-cyanophenol compound of formula VII

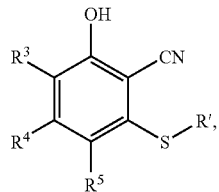

where R' is $C_1$-$C_6$-alkyl or benzyl and $R^3$, $R^4$ and $R^5$ are independently of one another selected from the group consisting of hydrogen, halogen, cyano, nitro, $C_1$-$C_6$-alkyl, $C_3$-$C_8$-cycloalkyl, $C_1$-$C_4$-haloalkyl, $C_1$-$C_4$-alkoxy, $C_1$-$C_4$-alkylthio, $C_1$-$C_4$-alkylsulfinyl, $C_1$-$C_4$-alkylsulfonyl, $C_1$-$C_4$-haloalkoxy, $C_1$-$C_4$-haloalkylthio, $C_2$-$C_6$-alkenyl, $C_2$-$C_6$-alkinyl, $C_1$-$C_4$-alkoxycarbonyl, amino, ($C_1$-$C_4$-alkyl)amino, di-($C_1$-$C_4$-alkyl)amino, aminocarbonyl, ($C_1$-$C_4$-alkyl)aminocarbonyl and di-($C_1$-$C_4$-alkyl)aminocarbonyl, comprising reacting a 2-methyl-3-nitro-phenylthioether of the formula VI

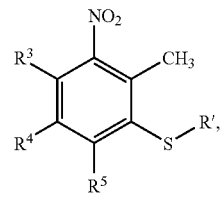

where R' is $C_1$-$C_6$-alkyl or benzyl and $R^3$, $R^4$ and $R^5$ are as defined above, with an organic nitrite R—ONO, wherein R is alkyl, in the presence of a base.

* * * * *